United States Patent [19]

Yoshimi et al.

[11] Patent Number: 4,572,207
[45] Date of Patent: Feb. 25, 1986

[54] PULSIMETER FOR VEHICLES

[75] Inventors: Tomohisa Yoshimi, Gamagori; Yuji Takeo, Toyokawa, both of Japan

[73] Assignee: Nippondenso Co., Ltd., Kariya, Japan

[21] Appl. No.: 593,947

[22] Filed: Mar. 27, 1984

[30] Foreign Application Priority Data

May 23, 1983 [JP] Japan .................................. 58-90509

[51] Int. Cl.$^4$ ................................................ A61B 5/04
[52] U.S. Cl. ..................................... 128/706; 128/639
[58] Field of Search ...................... 128/639, 689, 706; 340/586

[56] References Cited

U.S. PATENT DOCUMENTS

| 3,731,672 | 5/1973 | McIntosh | 128/639 |
| 3,858,574 | 1/1975 | Page | 128/689 |
| 4,223,683 | 9/1980 | Lown et al. | 128/706 |
| 4,319,581 | 3/1982 | Cutter | 128/639 |
| 4,444,200 | 4/1984 | Fujisaki et al. | 128/706 |

Primary Examiner—William E. Kamm
Attorney, Agent, or Firm—Cushman, Darby & Cushman

[57] ABSTRACT

A pulsimeter for a vehicle comprises electrodes and an electronic unit for measuring heart pulsation rate of a vehicle driver. The electrodes are provided on a steering wheel assembly of a vehicle so that, when the driver touches the electrodes with his hands, electrical potentials corresponding to the muscular activity of the driver's heart are picked up. The electronic unit differentially amplifies the electrical potentials and the interval of time between pulsation signals successively produced by the differential amplification is measured to obtain the driver's pulsation rate. The pulsation rate may be used for display or for some other purposes.

9 Claims, 8 Drawing Figures

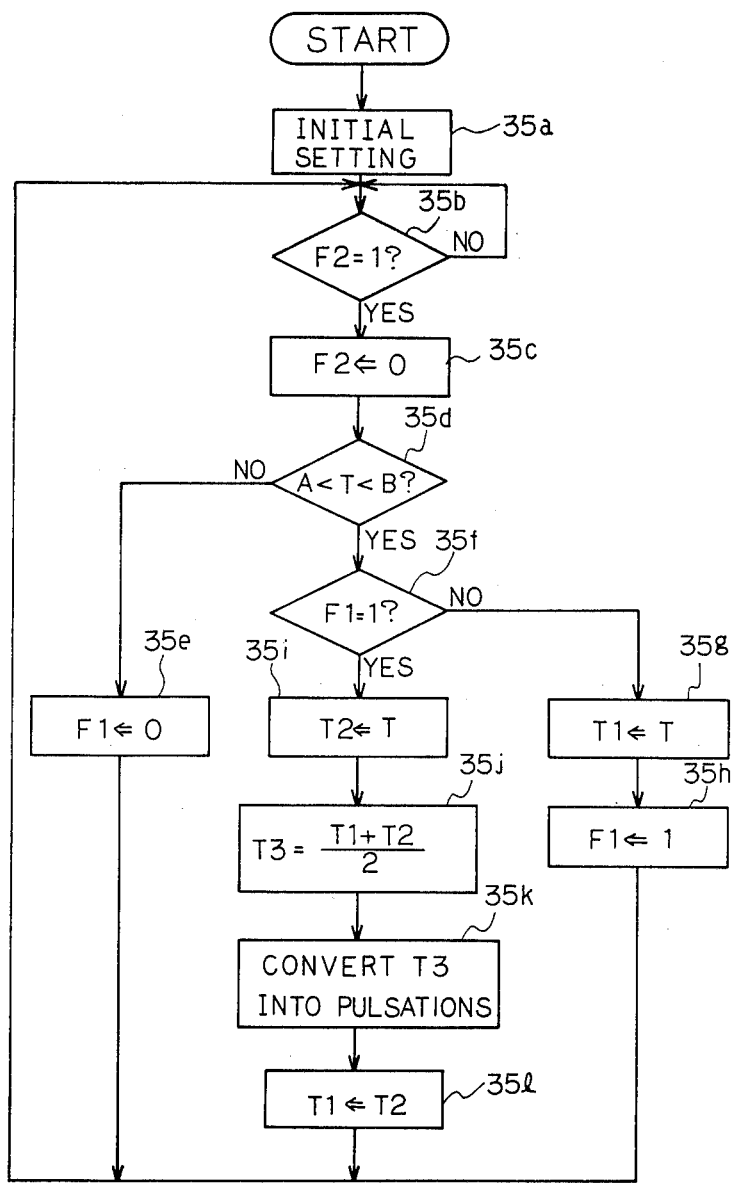

PULSIMETER FOR VEHICLES

BACKGROUND OF THE INVENTION

The present invention relates to pulsimeters. More specifically, the present invention provides a pulsimeter installed in a vehicle for measuring heart pulsation rate of a driver of the vehicle.

Heart pulsation rate (numer of heart beats/unit time) of a human being increases and decreases depending on his or her mental and/or physical condition and the driver's driving habits depend, more or less, on his mental and/or physical condition. Therefore it is desirable that the heart pulsation rate of the driver be measured and to either inform him of the measured pulsation rate or to brake or otherwise decelerate the vehicle automatically in response to the measured heart pulsation rate meeting certain predetermined conditions for promoting safe driving.

SUMMARY OF THE INVENTION

It is a primary object of the invention to provide a pulsimeter for vehicles which automatically measures heart pulsation rate of a vehicle driver.

It is a further object of the invention to provide a pulsimeter which can easily and effectively be installed in a vehicle.

In the present invention, electrodes electrically isolated from each other are provided on a steering wheel assembly of a vehicle. These electrodes are grasped by a vehicle driver so that electrical potentials corresponding to the muscular activity of the driver's heart are picked up from the driver's right and left hands based upon the first derivative principle. The electrical potentials picked up by the electrodes are differentially amplified and shaped into a pulse signal which corresponds to the muscular activity of the driver's heart ventricle. The interval of time between the pulse signals successively produced is measured to calculate the heart pulsation rate of the driver. The calculated pulsation number may be used for display or for some other purposes.

DETAILED DESCRIPTION OF THE PREFERRED EMBODIMENTS

Figure 1A:
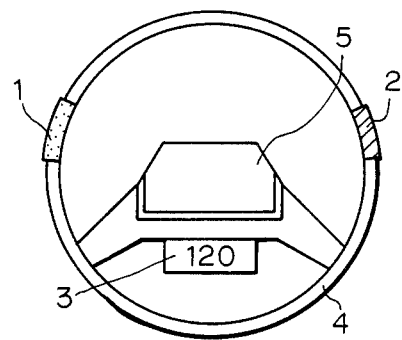
FIGS. 1A and 1B are pictorial views showing portions of a pulsimeter for vehicles according to a first embodiment of the invention.
Figure 1B:
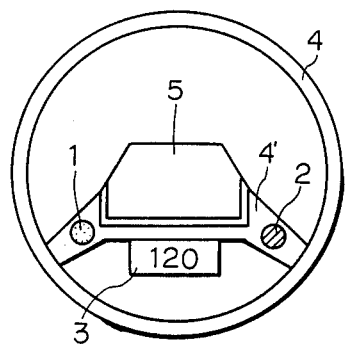

Referring first to FIGS. 1A and 1B showing a first embodiment of the invention, a pair of electrodes 1 and 2 are provided on a steering wheel 4 or on spokes 4' of the steering wheel 4 to be grasped with ease by a vehicle driver's left and right hands, respectively. The electrodes 1 and 2 are electrically insulated from each other by the wheel 4 or the spokes 4'. Electrodes 1 and 2 are most preferably made of materials having a low contact impedance and which are not very stimulative to human beings. The electrodes 1 and 2 may be secured to the wheel assembly by threads or may be coated on the wheel assembly. An electronic unit 3 is connected to the electrodes 1 and 2 by electric leads, not shown, and is provided adjacent to a horn switch 5 for measuring and displaying heart pulsation rate of the driver.

Figure 2A:
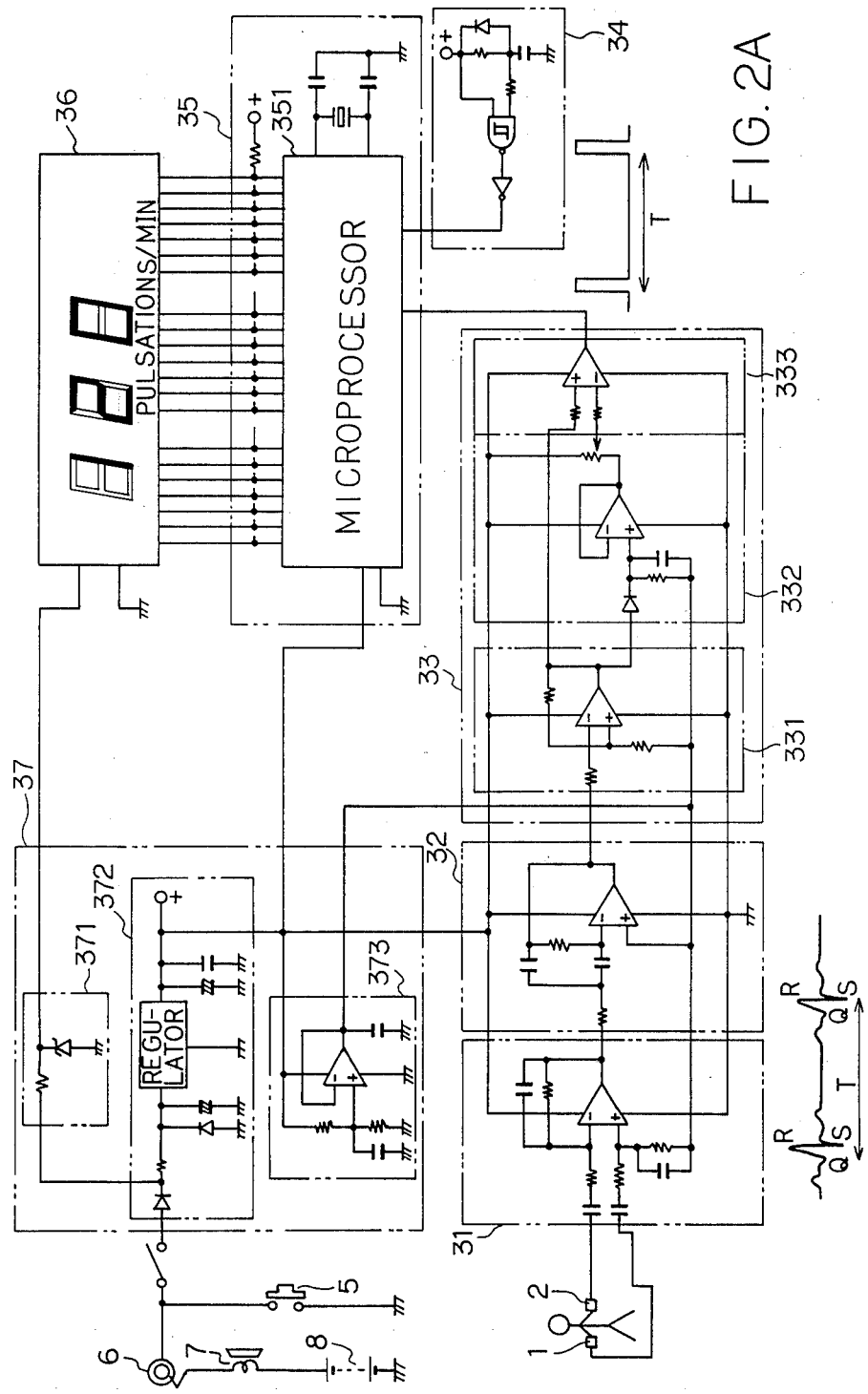
FIG. 2A is an electric schematic diagram of the circuitry of the pulsimeter shown in FIGS. 1A and 1B, and FIGS. 2B, 2C and 2D are flow charts showing a main routine, timer interrupt routine and pulse interrupt routine, respectively of a microprocessor shown in FIG. 2A.

Referring now to FIG. 2A there is shown a schematic diagram of electronic unit 3. An amplifier circuit 31 including an a.c. differential amplifier having a high input impedance is connected to the electrodes 1 and 2 for differentially amplifying electrical potentials picked up from the right and left hands of the driver through the electrodes 1 and 2 to provide a pulsation signal and for suppressing noise signals such as for example those induced by ignition of the vehicle. A band pass filter circuit 32 is connected to an output of amplifier circuit 31 for passing only a portion of the pulsation signal in a predetermined frequency range. The central frequency of the filter circuit 32 is preferably about 20 Hz in view of the fact that the pulsation signal mainly includes frequency components at about 20 Hz. A shaper circuit 33, including a non-inverting amplifier 331, a peak detector 332 and a voltage comparator 333 is connected to an output of filter circuit 32 for amplifying, peak-detecting and shaping the pulsation signal from the filter circuit 32 so that the pulsation signal is shaped into a pulse signal.

Figure 2C:
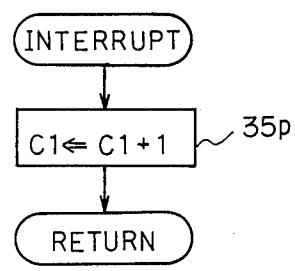
Figure 2D:
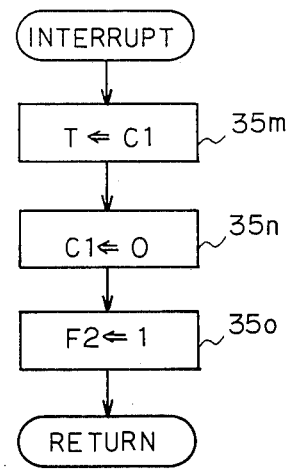

A calculator circuit 35 primarily including a microprocessor 351 programmed to execute routines shown in flow chart form in FIGS. 2B, 2C and 2D is connected to the shaper circuit 33 for calculating pulsation number per unit time (heart rate) by measuring the interval of time between the pulse signal successively applied from the shaper circuit 33. The calculator circuit 35 is connected to a reset circuit 34 which produces a reset signal when a voltage is applied thereto. A display circuit 36 is connected to the calculator circuit 35 for numerically displaying the calculated pulsation rate on the steering wheel assembly.

A voltage supply circuit 37 including voltage regulators 371, 372 and 373 is connected to the electric lead which connects the horn switch 5 to a slip ring 6 connected to a battery 8 through a horn 7. The volatge supply circuit 37, receiving a voltage from the battery 8 through the slip ring 6, regulates the same and supplies regulated voltages required by the circuits 31, 32, 33, 34, 35 and 36 described above.

The operation of the pulsimeter accoring to the first embodiment shown in FIGS. 1A, 1B and 2A is described next with further reference to flow charts shown in FIGS. 2B, 2C and 2D.

Assuming that the vehicle driver is grasping or touching the electrodes 1 and 2 by his or her left and right hands, respectively, while driving a vehicle, electric potentials corresponding to the muscular activity of the driver's heart are picked up by the electrodes 1 and 2 through his or her left and right hands and then differentially ampliflied by the amplifier circuit 31. Thus, a pulsation signal having a waveform QRS which corresponds to a muscular activity of the driver's heart ventricle and has a relatively large magnitude is produced. The pulsation signal is applied to the shaper circuit 33 through the filter circuit 32. In the shaper circuit 33, the pulsation signal is amplified by the amplifier 331, the peak level R of the pulsation signal is detected by the peak detector 332 and the pulsation signal from the amplifier 331 is compared with a reference level proportional to the detected peak level by the voltage comparator 333 so that the pulsation signal is shaped into the pulse signal.

The calculator circuit 35, more particularly the microprocessor 351, being reset by the reset circuit 34, executes the main routine, timer interrupt routine and pulse interrupt routine shown in FIGS. 2B, 2C and 2D, respectively.

In the main routine shown in FIG. 2B, initial setting is executed at a step 35a to reset flags F1(F1=0), F2(F2=0), clock count value C1(C1=0), and time interval values T1(T1=0), T2(T2=0), T3(T3=0) which will be described later. At the initial setting, the frequency of a reference clock (not shown) is determined to be 10 Hz so that the timer interrupt routine shown in FIG. 2C is executed at every 0.1 second. Thus a clock count value C1 of reference clock is incremented by one at every 0.1 second at a step 35p in the timer interrupt routine.

After the step 35a in the main routine, it is determined at a step 35b if the flag F2 is set (F2=1) by the pulse signal from the shaper circuit 33. If no pulse is applied, the flag F2 is maintained reset (F2=0) and no further step which follows the step 35b is executed.

When the pulse signal is applied from the shaper circuit 33, the pulse interrupt routine shown in FIG. 2D is executed at a step 35m. The clock count value C1 at the moment is stored as the interval of time T between the pulse signals previously and currently applied. Then the count value C1 is reset (C1=0) at a step 35n for the next calculation of the time interval T and the flag F2 is set (F2=1) at a step 35o to indicate that the pulse signal is applied.

After the pulse interrupt routine, the main routine is resumed and, after the step 35b in which it is determined that the flag F2 is set (F2=1), a step 35C is executed to reset the flag F2(F2=0). Then the time interval T obtained in the pulse interrupt routine is compared with constants A and B at a step 35d. For example, the constants A and B may be 3 and 15, respectively, which correspond to 200 and 40 heart beats per minute so as to cover a range of all possible heart rates of human beings. If the time interval T is not within a range between the constants A and B, a step 35e is executed to reset the flag F1(F1=0) so that the time interval T which is considered abnormal is not used any more. If the time interval T is within the range between the constants A and B, a step 35f is executed to discriminate if the flag F1 is set (F1=1), or if the previous time interval T is available or not.

With the flag F1 being reset (F1=0) to indicate the unavailability of the time interval T1 obtained previously, the time period T is stored as T1 at a step 35g and the flag F1 is set at a step 35h to indicate the availability of the time interval T1. With the flag F1 being set (F1=1) to indicate the availability of the previously obtained time interval T1, on the contrary, the step 35f is followed by a step 35i.

At the step 35i, the time interval T is stored as the current time interval T2. Then an average time interval T3 is obtained by the use of the previous and current time intervals T1 and T2 at a step 35j and, at a step 35k the average time interval T3 is converted into the pulsation number per minute to be displayed. After the step 35k, the current time interval T2 is stored as the previous time interval T1 to be used next time again.

The above-described routines are repeated and the pulsation number per minute is displayed by the display circuit 36, thus enabling the vehicle drive to know his or her heart pulsation.

Figure 3:
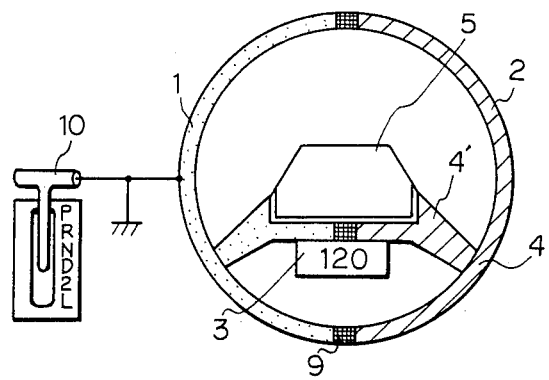
FIG. 3 is a pictorial view showing portions of a pulsimeter for vehicles according to a second embodiment of the invention.

Referring to FIG. 3 there is shown a second embodiment of the invention. Electrodes 1 and 2 are provided to cover substantially whole area of the wheel 4 and spokes 4' but electrically insulated from each other by an insulator 9. One of the electrodes, the electrode 1, is electrically grounded to vehicle chassis and a transmission shift lever 10 provided with another electrode is also electrically grounded to the vehicle chassis. The electrodes 1 and 2 may be connected to the electronic unit as shown in FIG. 2A.

The second embodiment operates in the same manner as in the first embodiment as long as the vehicle driver holds or touches the electrodes 1 and 2 by his or her left and right hands. It should be noted, however, that the pulsation of the vehicle driver is also measured even when he or she holds or touches the shift lever 10 by one hand with the other hand touching the electrode 2.

Figure 4:
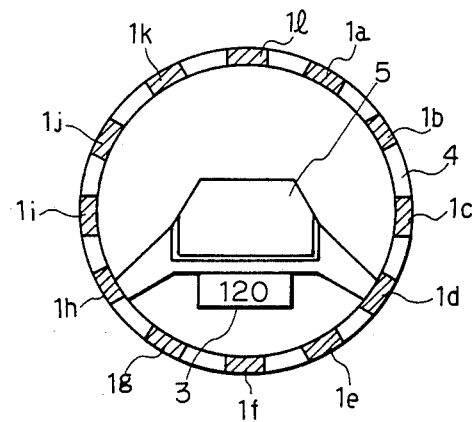
FIG. 4 is a pictorial view showing portions of a pulsimeter for vehicles according to a third embodiment of the invention.

Referring to FIG. 4 there is shown a third embodiment of the invention. A plurality of electrodes 1a through 1l electrically separated from each other, are provided on the steering wheel 4 so that the pulsation rate of the driver may be measured substantially whenever the driver's hands are on the steering wheel 4. As one example, one half of the electrodes 1a, 1c, 1e, 1g, 1i, 1k and the other half of the electrodes 1b, 1d, 1f, 1h, 1j, 1l may be connected to the inverting and non-inverting inputs of the amplifier circuit 31 of the electronic unit 3 shown in FIG. 2A, respectively.

It should be noted that the present invention is not limited to the embodiments described above but may be modified in various ways without departing from the spirit of the invention. For example, actual number of pulse signals may be measured to measure the heart pulsation rate, and alarming or automatic vehicle braking may be effectuated when the pulsation rate of the driver decreases because of for example the driver falling asleep.

What we claim is:

1. A pulsimeter for a vehicle having a steering wheel assembly including a slip ring and horn switch comprising:

first and second electrodes, provided on said steering wheel assembly and electrically separated from each other, for picking up electrical potentials when touched by a driver's right and left hands respectively corresponding to muscular activity of a driver's heart;

first circuit means, connected to said electrodes, for differentially amplifying said electrical potentials picked up by said electrodes and providing an output signal corresponding to each heart beat of the driver;

second circuit means, connected to said first circuit means, for calculating the driver's heart pulsation rate by measuring the interval of time between said output signals successively produced by said first circuit means, said second circuit means including microprocessor means for averaging intervals of time from one pulsation to the next successively measured and calculating said pulsation rate therefrom, the microprocessor means including means for discriminating whether each interval is within a predetermined range or not, the averaging means averaging only those intervals within said predetermined range;

display means, connected to said second circuit means and provided on said steering wheel assembly, for displaying said calculated rate; and voltage supply means, connected to an electric lead connecting said slip ring and horn switch for supplying power to said first and second circuit means and display means.

2. A pulsimeter according to claim 1, wherein said electrodes are provided on a steering wheel of said steering wheel assembly.

3. A pulsimeter according to claim 1, wherein said electrodes are provided on steering wheel spokes of said steering wheel assembly.

4. A pulsimeter according to claim 1, wherein one of said electrodes is grounded.

5. A pulsimeter according to claim 4 further comprising:

a third electrode electrically connectable to either said first or second electrode provided on a transmission shift lever of said vehicle.

6. A pulsimeter according to claim 1 further comprising:

voltage supply means, connected to an electric lead connecting a slip ring and a horn switch provided on said steering wheel assembly, for supplying said first circuit means, said second circuit means and said display means with operating power.

7. A pulsimeter according to claim 6, wherein said first circuit means includes:

an a.c. differential amplifier, connected to said electrodes, for differentially amplifying said electrical potentials; and a filter, connected to said amplifier, for passing only output signals of said amplifier which are in a predetermined frequency range, the central frequency of said predetermined frequency range being at about 20 Hz.

8. A pulsimeter according to claim 7, wherein said first circuit means further includes:

a voltage comparator, connected to said filter, for comparing an output signal of said filter with a reference signal to produce a pulse signal as said output signal of said first circuit means.

9. A pulsimeter according to claim 8, wherein said first circuit means further includes:

a peak detector, connected to said filter, for detecting a peak level of said output signal of said filter and producing said reference signal having a signal level proportional to the detected peak level.

* * * * *